US010973409B2

(12) United States Patent
Kiderman et al.

(10) Patent No.: US 10,973,409 B2
(45) Date of Patent: Apr. 13, 2021

(54) OBJECTIVE TESTING OF VERGENCE DYSFUNCTION FOR USING DYNAMIC VERGENCE TESTING PLATFORM INCLUDING 3D HEAD MOUNTED DISPLAY SYSTEM WITH INTEGRATED EYE TRACKING TECHNOLOGY

(71) Applicant: Neuro Kinetics, Inc., Pittsburgh, PA (US)

(72) Inventors: Alexander D. Kiderman, Pittsburgh, PA (US); Robin C. Ashmore, Pittsburgh, PA (US)

(73) Assignee: NEURO KINETICS, Pittsburgh, PA (US)

( * ) Notice: Subject to any disclaimer, the term of this patent is extended or adjusted under 35 U.S.C. 154(b) by 58 days.

(21) Appl. No.: 16/109,485

(22) Filed: Aug. 22, 2018

(65) Prior Publication Data

US 2019/0082954 A1   Mar. 21, 2019

Related U.S. Application Data

(63) Continuation-in-part of application No. PCT/US2017/018862, filed on Feb. 22, 2017.
(Continued)

(51) Int. Cl.
*A61B 3/113*   (2006.01)
*A61B 3/00*   (2006.01)
(Continued)

(52) U.S. Cl.
CPC ............ *A61B 3/113* (2013.01); *A61B 3/0041* (2013.01); *G02B 27/0093* (2013.01); *G02B 27/017* (2013.01)

(58) Field of Classification Search
CPC ....... A61B 3/00; A61B 3/0008; A61B 3/0091; A61B 3/08; A61B 3/085
See application file for complete search history.

(56) References Cited

U.S. PATENT DOCUMENTS 7,988,287 B1 * 8/2011 Butler .................. A61B 3/1015
351/210
8,568,311 B2   10/2013 LaPlaca et al.
(Continued)

FOREIGN PATENT DOCUMENTS

WO   2015051272   4/2015

OTHER PUBLICATIONS

Gopher, Daniel et al. Flying with dichoptic displays: the interplay between display characteristics and attention control, proceedings of the human Factors Society 36th Annual Meeting, 1992. pp. 1469-1473, "Method", paragraph 2, "Discussion", paragraph 1: Abstract.

*Primary Examiner* — Robert E. Tallman
(74) *Attorney, Agent, or Firm* — Blynn L. Shideler; Krisanne Shideler; BLK Law Group

(57) ABSTRACT

An objective testing of vergence dysfunction comprising the steps of: providing a head mounted goggle based stimulus generating eye tracking unit to the subject; presenting visual stimulus to the subject, wherein the visual stimulus is in the head mounted goggle based system and forms the optical target stimulus for at least one vergence test; obtaining objective physiologic response of the subject from the head mounted goggle unit based upon each of the visual stimulus presented to the subject in each test; and using the objective physiologic responses to diagnose the presence of vergence dysfunction. On objective portable head mounted goggle based stimulus generating eye tracking unit for vergence testing is discloses as is a method of method of vergence recovery convalescence.

18 Claims, 5 Drawing Sheets

Related U.S. Application Data

(60) Provisional application No. 62/298,304, filed on Feb. 22, 2016.

(51) Int. Cl.
*G02B 27/00* (2006.01)
*G02B 27/01* (2006.01)

(56) References Cited

U.S. PATENT DOCUMENTS

| | | |
|---|---|---|
| 8,585,609 B2 | 11/2013 | Kiderman et al. |
| 9,039,632 B2 | 5/2015 | Kiderman et al. |
| 2010/0094161 A1 | 4/2010 | Kiderman et al. |
| 2010/0280372 A1 | 11/2010 | Poolman et al. |
| 2014/0192326 A1 | 7/2014 | Kiderman et al. |
| 2014/0327880 A1 | 11/2014 | Kiderman et al. |
| 2015/0335278 A1 | 11/2015 | Ashmore et al. |
| 2016/0262608 A1* | 9/2016 | Krueger ................ G06T 19/006 |
| 2016/0270711 A1 | 9/2016 | Ashmore et al. |

* cited by examiner

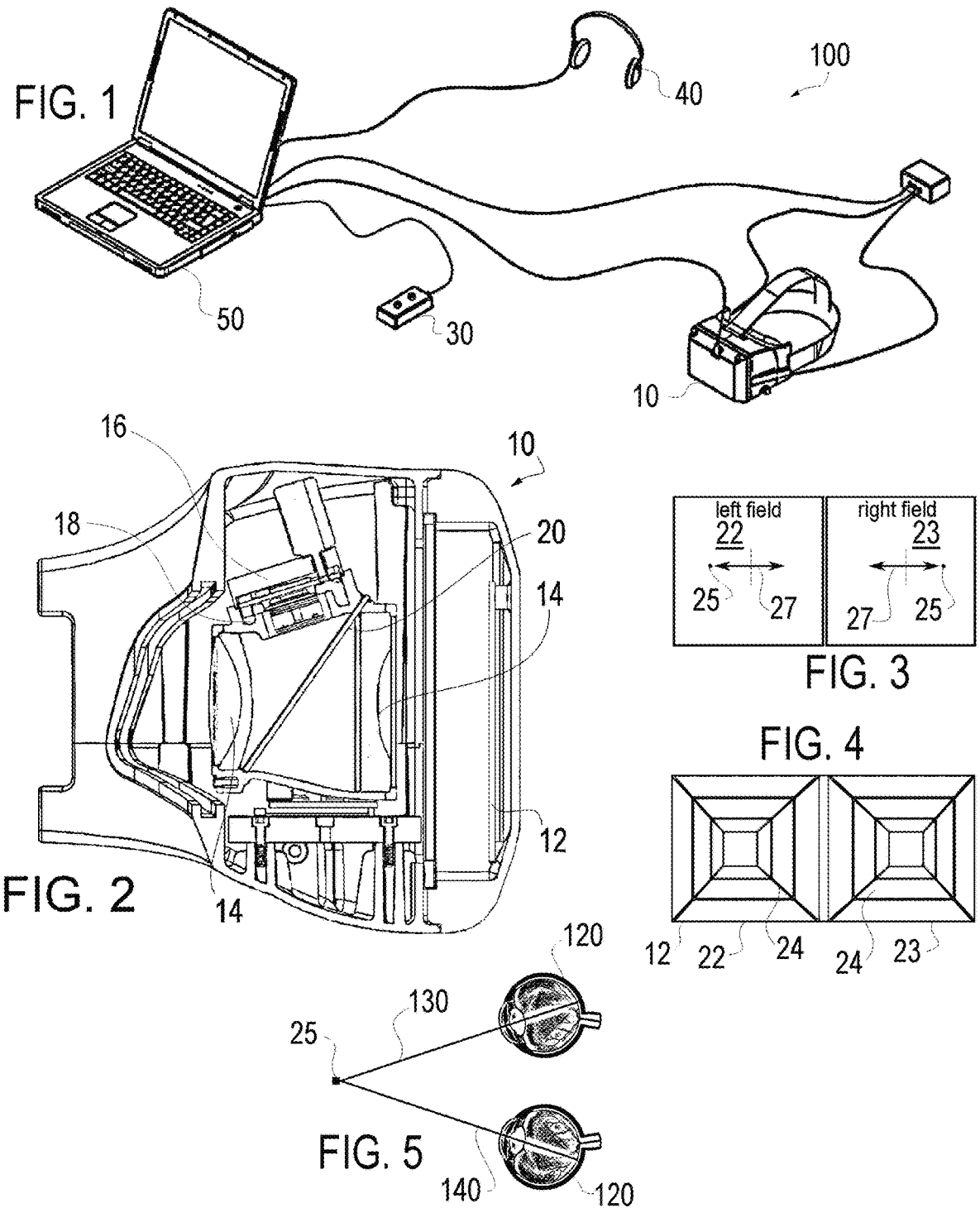

Disparity Fusion Test, Decay Time

|  | Inward Target Movement | | Outward Target Movement | | Inward Target Movement | | Outward Target Movement | |
|---|---|---|---|---|---|---|---|---|
|  | Decay Time, sec | | Decay Time, sec | | Eye amplitude, deg. | | Eye amplitude, deg. | |
| Subjects | L | R | L | R | L | R | L | R |
| mTBI | 1.34 | 1.34 | 1.48 | 0.96 | 0.6 | 0.46 | 0.22 | 0.52 |
| Control | 0.45 | 0.49 | 0.29 | 0.35 | 2.21 | 2.26 | 1.43 | 1.56 |

|  | Near angle, deg | | Far angle, deg | | Excursion | | Excursion ratio | Symmetry | Near lag, sec | | Far lag, sec | |
|---|---|---|---|---|---|---|---|---|---|---|---|---|
| Subjects | L | R | L | R | L | R |  |  | L | R | L | R |
| mTBI | 0.10 | -0.39 | -0.10 | 0.39 | 0.20 | 0.78 | 0.26 | 0.94 | 1.37 | -5.36 | 1.34 | 4.67 |
| Control | 1.68 | -1.87 | -1.63 | 1.78 | 3.31 | 3.65 | 0.91 | -0.99 | 0.1 | 0.12 | 0.06 | 0.07 |

|  | mTBI group (*n*=17) | Control group (*n*=58) | LSD p-value (Kruskal-Wallis p) |
|---|---|---|---|
| Disparity fusion (vergence saccade) symmetry | -0.22 ± 0.18 | -0.86 ± 0.03 | p<0.001 (p<0.001) |
| Vergence smooth pursuit symmetry | -0.43 ± 0.17 | -0.94 ± 0.03 | p<0.001 (p<0.002) |

Logistic Regression Analysis
Disparity Fusion (Vergence Saccade)

| Observed | | | Predicted | | |
|---|---|---|---|---|---|
| | | | Concussion | | Percentage Correct |
| | | | No | Yes | |
| Step 3 | Concussion | No | 55 | 3 | 94.8 |
| | | Yes | 7 | 10 | 58.8 |
| | Overall Percentage | | | | 86.7 |

Key Factors
- Inward Symmetry
- Inward Amplitude
- Outward Saccade

FIG. 13

Logistic Regression Analysis
Vergence Smooth Pursuit

| Observed | | | Predicted | | |
|---|---|---|---|---|---|
| | | | Concussion | | Percentage Correct |
| | | | No | Yes | |
| Step 2 | Concussion | No | 58 | 0 | 100.0 |
| | | Yes | 9 | 8 | 47.1 |
| | Overall Percentage | | | | 88.0 |

Key Factors
- Symmetry
- Near and Far Lag

OBJECTIVE TESTING OF VERGENCE DYSFUNCTION FOR USING DYNAMIC VERGENCE TESTING PLATFORM INCLUDING 3D HEAD MOUNTED DISPLAY SYSTEM WITH INTEGRATED EYE TRACKING TECHNOLOGY

RELATED APPLICATIONS

This application is a continuation in part of International Patent Application Serial Number PCT/US17/018862 filed Feb. 22, 2017 and published as publication number WO 2017-147141, which application and publication are incorporated herein by reference. International Patent Application Serial Number PCT/US17/018862 claims the benefit of U.S. Patent Application 62/298,304 filed Feb. 22, 2015 entitled "Dynamic Vergence Testing Platform Including 3D Head Mounted Display System with Integrated Eye Tracking Technology for Objective Testing of Vergence Dysfunction for Diagnosis and Vergence Recovery for Convalescence."

BACKGROUND OF THE INVENTION

1. Field of the Invention

The present invention relates to vergence testing, and more specifically to quantitative, noninvasive, clinical objective testing of vergence dysfunction for diagnosis and vergence recovery for convalescence. The present invention is also directed to noninvasive rapid dynamic vergence testing platform including 3d head mounted display system with integrated eye tracking technology and methods of using the same.

2. Background Information

Traumatic Brain Injury (TBI) is the result of a blunt blow, jolt or blast overpressure to the head that disrupts brain function. The subset of mild TBI, or mTBI, has represented a harder segment of TBI to diagnose. Within this application mTBI is a subset of TBI. The terms mild TBI (mTBI) and concussion are commonly used interchangeably in the art, and have been linked with Post Traumatic Stress Disorder. The severity of head injuries range from a brief change in mental status or consciousness to extended unconsciousness and amnesia. In severe or multiple concussion cases, personality changes can occur with devastating results.

The Centers for Disease Control and Prevention previously estimated that at least 3.17 million Americans currently have a long-term or lifelong need for help to perform activities of daily living as a result of a TBI. Currently there are few accepted clinical methods to detect mTBI. The Center for Disease Control (at http://www.cdc.gov/TraumaticBrainInjury/statistics.html) estimates that "About 75% of TBI's that occur each year are concussions or other forms of mild TBI." For further background consult the Brain Injury Association of America at www.BIAUSA.org. The Brain Injury Association of America (BIAA) is the country's oldest and largest nationwide brain injury advocacy organization.

Proper treatment of TBI injury requires an accurate diagnosis of the structures affected. Neurosensory symptoms, including oculomotor and vestibular (dizziness and balance) disorders, are among the most common disabilities seen after injury. Proper treatment of TBI injury requires an accurate diagnosis of the structures affected. The mechanisms of injury in TBI cause a variety of abnormalities in the peripheral vestibular mechanisms, central vestibular structures, ocular-motor tracts, cerebellum, as well as all portions of the brain communicating with these structures. Despite their prevalence, these symptoms and deficits can be difficult to quantify.

Existing screening and diagnostic tools for mTBI in general which are employed on patients and which are based on the traditional battery of vestibular, balance and neurological tests often requires the use of large stationary systems (neuro-otologic test center, Barany/rotary chair, ENG/VNG, computerized posturography/balance platforms, etc.). These large systems deploy a full battery of ocular motor, motion, artificial motion, balance and combined tests. Utilizing such devices may be practical in hospital settings, but are not useful in forward deployed military settings, or remote locations, such as first responder emergency medical technicians (EMTs).

Vergence is an oculomotor function, described as disconjugate movement of the eyes to track objects varying in depth over the binocular visual field, and is commonly affected following mTBI. Convergence insufficiency, determined by static measures of vergence function, has long been known to result from mTBI specifically a receded near point of convergence amplitude; a decreased compensatory fusional ranges at near; and abnormal phoria at near or far (horizontal, vertical).

Further background on TBI assessment systems is disclosed in U.S. Pat. No. 8,568,311 developed by Emory University which discloses an immersive cognitive assessment system which suppresses outside video and audio inputs. The '311 patent, which is incorporated herein by reference, discloses a distinct approach to the TBI assessment from that the present development but is helpful to further establish the state of the art, including a relatively comprehensive listing of publications in the field.

Additional background on mTBI assessment systems is disclosed in International Patent Publication WO 2015-051272 developed by Indiana University (Nicholas L. Port—Inventor) which confirms the validity of vergence testing (along with other parameters) for TBI diagnosis but yet develops a distinct battery of tests for mTBI diagnosis which include "a self-paced saccade test, a sinusoidal pursuit test, a step ramp pursuit test and ocular following task and a dynamic random dot task". The '272 publication, which is incorporated herein by reference, thus teaches a distinct approach to the TBI assessment from that of the present development but is helpful to further establish the state of the art.

Additionally the applicants have developed noninvasive rapid screening of mild traumatic brain injury using combination of subject's objective oculomotor, vestibular and reaction time analytic variables set forth in publication number 2015-0335278. See also Publication No. 2016-0270711, Publication No. 2014-0327880 and related U.S. Pat. No. 9,039,632; Publication No. 2014-0192326 and related U.S. Pat. No. 9,039,631; and U.S. Publication Number 2010-0094161 and related U.S. Pat. No. 8,585,609, each of which patents and publications are incorporated herein by reference.

It is the object of the present invention to address the deficiencies of the prior art to yield noninvasive rapid dynamic vergence testing platforms.

SUMMARY OF THE INVENTION

The present invention is drawn to the development of a portable virtual reality device that will facilitate the effective and efficient noninvasive rapid dynamic vergence testing by forming a platform including 3d head mounted display system with integrated eye tracking technology for quantitative, noninvasive, clinical objective testing of vergence dysfunction for diagnosis and vergence recovery for convalescence. Vergence is an oculomotor function comprising disconjugate movement of the eyes to track objects varying in depth over the binocular visual field.

The summary of the present invention is three fold. First, concussed patients present with a profile of vergence deficits can be measured objectively with a non-invasive, portable system or platform of the present invention. Further that objective vergence data may be used as a tool in mTBI diagnosis and finally that objective vergence testing can be used to monitor, track and facilitate mTBI recovery.

One aspect of the invention provides invention provides an objective testing of vergence dysfunction comprising the steps of: providing a head mounted goggle based stimulus generating eye tracking unit to the subject; presenting visual stimulus to the subject, wherein the visual stimulus is in the head mounted goggle based system and forms the optical target stimulus for at least one vergence test; obtaining objective physiologic response of the subject from the head mounted goggle unit based upon each of the visual stimulus presented to the subject in each test; and using the objective physiologic responses to diagnose the presence of vergence dysfunction.

One aspect of the invention provides an portable objective testing platform for vergence testing which may be summarized as including a laptop; and a head mounted goggle based stimulus generating eye tracking unit coupled to the laptop, the unit including a VR screen and two cameras for recording eye movement, wherein the VR screen is configured to present visual stimulus to the subject, wherein the visual stimulus is in the head mounted goggle based system and forms the optical target stimulus for at least one vergence test, and wherein the cameras are configured to obtain objective physiologic responses of the subject from the head mounted goggle unit based upon each of the visual stimulus presented to the subject in each test.

Another aspect of the present invention is the provision of vergence recovery convalescence using the dynamic vergence testing platform including 3d head mounted display system with integrated eye tracking technology comprising the steps of: A. providing a head mounted goggle based stimulus generating eye tracking unit to the subject; B. presenting visual stimulus to the subject, wherein the visual stimulus is in the head mounted goggle based system and forms the optical target stimulus for at least one vergence test; C. obtaining objective physiologic response of the subject from the head mounted goggle unit based upon each of the visual stimulus presented to the subject in each test; and D. Presenting at least select physiologic response to the subject; and E. Repeating steps B-D.

These and other advantages are described in the brief description of the preferred embodiments in which like reference numeral represent like elements throughout.

BRIEF DESCRIPTION OF THE FIGURES

FIG. 1 is a schematic view of the dynamic vergence testing platform including 3d head mounted display system with integrated eye tracking technology for objective testing of vergence dysfunction for diagnosis and vergence recovery for convalescence;

FIG. 2 is a schematic view of the 3d head mounted display system of the vergence testing platform of FIG. 1;

FIG. 3 schematically illustrates the creation of a vergence target in the head mounted display system of the vergence testing platform of FIG. 1;

FIG. 4 schematically illustrates a background used to facilitate vergence testing in the head mounted display of the vergence testing platform of FIG. 1;

FIG. 5 schematically illustrates vergence testing physiology;

FIG. 11 is a chart summarizing symmetry results for mTBI subjects and control subjects for a series of vergence testing performed on the head mounted display of the vergence testing platform of FIG. 1;

FIGS. 12 and 13 are charts summarizing linear regression analysis as a predictor of mTBI using the results of the vergence testing performed on the head mounted display of the vergence testing platform of FIG. 1.

DESCRIPTION OF THE PREFERRED EMBODIMENTS

Figure 6:
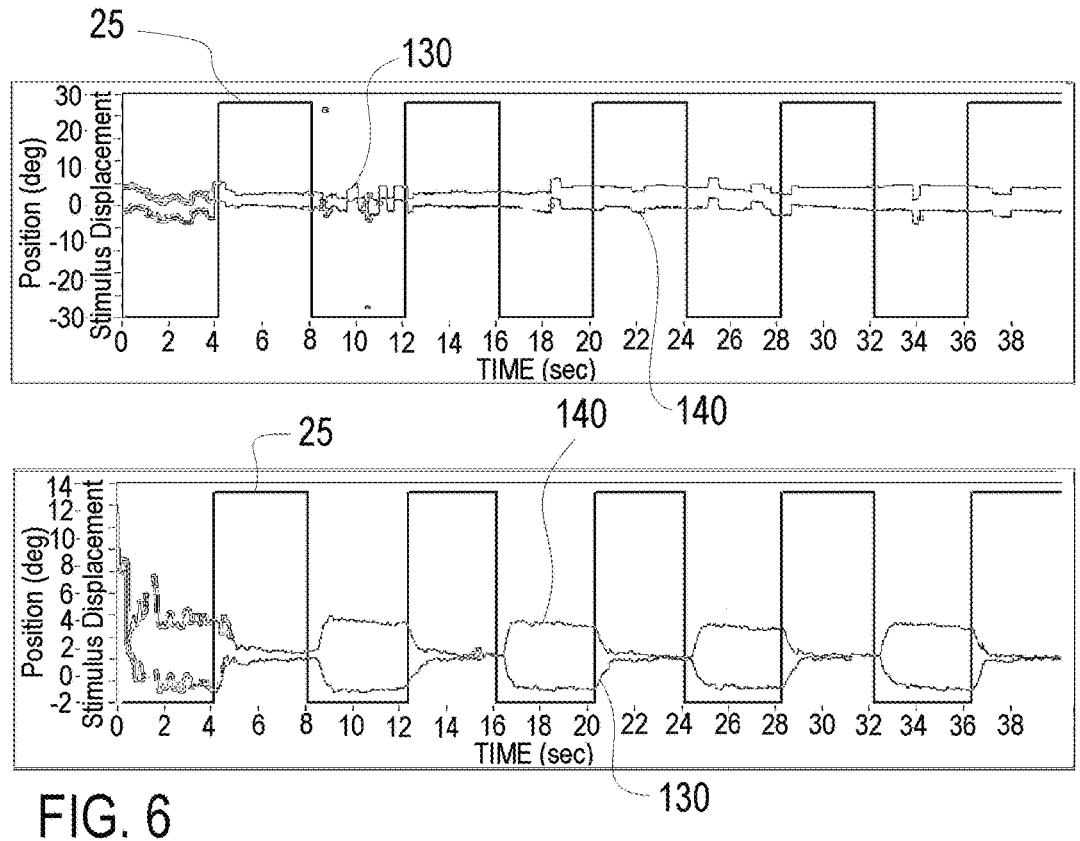
FIG. 6 is a graph of mTBI subject and control subject response to a vergence saccade test performed on the head mounted display of the vergence testing platform of FIG. 1.

It is noted that, as used in this specification and the appended claims, the singular forms "a," "an," and "the" include plural referents unless expressly and unequivocally limited to one referent. Within the following description the terms horizontal and vertical are relative to the conventional position of the subject's eyes/vision, regardless of the subject's actual head position, unless otherwise stated. Namely the subject's eyes and the center of the subject's vision will generally lie upon a horizontal plane (discounting variations in subject eye position for defining these reference directions). The vertical direction is perpendicular to the horizontal extending generally in the plane including the subject's chin and the top of their head. Regarding to the subject invention, there is mounting evidence to support the theory that vergence dysfunction contributes to disability after mTBI. Similarly there is mounting evidence to support the theory that vergence recovery is an important aspect in mTBI convalescence.

The platform or system 100 of the present invention may be categorized as a type of Video-oculography (VOG) system. VOG systems have been defined by Richard E. Gans, PhD, who is the Founder and Executive Director of the American Institute of Balance and he served on the board of the American Academy of Audiology, in the Hearing Journal: May 2001-Volume 54-Issue 5-pp 40, 42 "Video-oculography is a method of recording eye movement through the use of digital video cameras. This is a significant change from electronystagmography, which uses the corneal retinal potential, which is the eye's battery-like effect. As the eyes move side to side and up and down, the corneo-retinal potential's positive and negative discharge is recorded. VOG technology, however, uses infrared cameras to measure the eye's position. Small cameras, mounted in goggles, track the center of the pupil to provide the location of the eye." Specifically the platform is formed on the I-Portal®—PAS (Portable Assessment System, manufactured and supported by NKI Pittsburgh), a portable 3D head mounted display (HMD) system with integrated eye tracking technology. This technology is unique because it tests oculomotor and vergence function in an entirely virtual environment.

Videonystagmograpy (VNG) is often defined as a technology for testing inner ear and central motor functions, a process known as vestibular assessment and is defined as involving the use of infrared cameras to trace eye movements during visual stimulation and positional changes. A VNG unit is typically a diagnostic system for recording, analyzing and reporting (generally) involuntary eye movements, called nystagmus for involuntary movements, using video imaging technology. The eye tracking unit 100, as described in greater detail below, may also be defined as a VNG system 100. VNG systems 100 are considered, for the purpose of this application, to be a subset of the broader VOG terminology FIG. 1 is a schematic view of the dynamic vergence testing platform or system 100 including 3d head mounted display system 10 with integrated eye tracking technology for objective testing of vergence dysfunction for diagnosis and vergence recovery for convalescence. The system 100 includes the head mounted goggle unit 10, user input device 30, headphones 40 for auditory input for instructions or stimulus and/or subject isolation, coupled to a laptop 50 to yield a highly portable system.

The VOG/VNG system 100 is coupled to the subject and configured to present a plurality of virtual reality based visual stimulus to the subject, at least one visual stimulus providing a target stimulus for a visual based neurologic vergence testing. The system 100 is designed to obtain objective physiologic response of the subject from the eye tracking unit based upon the neurologic vergence test associated with each vergence visual stimulus presented to the subject. The system 100 is configured to use the objective physiologic responses to the neurologic vergence tests to diagnose the presence of traumatic brain injury.

Virtual environment exposure, also called virtual reality or VR, has proven highly efficient and effective in vestibular rehabilitation since the experience gained during VR exposure is transferable to the real world. The VR technology in the present invention is used to provide a visual target for performing a variety of vergence neurologic tests on the subject. Additionally, the VR use in the rehabilitation of TBI accelerates the compensation of an acute loss of peripheral or central vestibular function by improving adaptive modifications of the vestibulo-ocular reflex. The portable system 100 has the potential of being used bedside and in the home to increase rehabilitation compensation speed and degree.

FIG. 2 is a schematic design of head mounted VOG/VNG goggle unit 10 with OLED micro display or VR screen 12, two sets of optics 14, cameras 16 for recording eye movement typically at above 100 hz for vergence testing, micro LEDs 18 for illumination of the eyes, and a hot mirror. Simply, the VR screen 12 provides the visual stimulus and the cameras 16 capture eye response for quick analysis. The details of the VR display screen 12 are believed to be known to those or ordinary skill in the art and it allows the system 100 to present visual images or targets to the user that have a perceived or simulated distance for vergence testing. The eye tracking technology described herein, outside of the vergence testing described herein, is generally known in the art, and the camera based eye tracking goggle based unit 10 may use the IPORTAL® brand goggle based eye tracking cameras and software available from the assignee of this invention.

The combination of the eye tracking and the display of simulated distanced visual targets allow the VOG/VNG system 100 to automatically run a number of preprogrammed neurologic vergence tests and to record the physiologic responses thereto. Although generally known in the art, FIG. 3 schematically illustrates the creation of a target 25 for vergence testing in the unit 10 in which the screen 12 is divided into a left eye vision field 22 and a right eye vision field 23. The actual movement, for example along path 27, of the target stimuli 25 in the two fields 22 and 23 is presented separately to each eye. The target 25 moves horizontally outward (left in the left field, rightward in the right field) simultaneously, or inward (both toward the nasal center line), with respect to any fixed position in the two fields 22 and 23. This movement creates the perception of virtual depth, and when tracked by the two eyes, creates convergence and divergence eye movements for vergence testing.

FIG. 4 schematically illustrates a background 24 used to facilitate vergence testing in the head mounted display 10 of the vergence testing platform 100 of the invention, wherein to enhance the subjective experience of depth, and thereby increase the likelihood of subjects responding with appropriate convergence and divergence eye movements, stimuli 25 will be presented in the context of background stimuli 24 that will themselves appear as 3 dimensional objects that surround or encompass or otherwise orient the target stimulus in a virtual 3 dimensional space. For instance, the target 25 can move within a square tunnel 24 that has virtual depth. The background square tunnel 25 will have slight differences in the two images in the two fields 22 and 23, with increasing disparity near the center, which better creates the perception of a field that is farther from the viewer in the center than near the edges. Additionally the present invention contemplates the use of varying the size of the target 25, in order to maintain perspective and to simulate the normal reduction in size of distant objects relative to closer objects.

FIG. 5 schematically illustrates vergence testing physiology. The device 10 will present stimuli forming target 25 to each eye 120 (in this figure), each controlled independently, to simulate varying depth targets 25. Targets 25 can be, for instance, single dot targets, images, or any other visual stimulus that may be rendered on the screen 12. Through the varying of the horizontal shift of each eye's targets independently, an impression of varying depth is created for the target 25 as the subject converges their eyes 120 (see right eye position or trace 130 and left eye position or trace 140) on the independent targets and fuses the two images into a perceived single image or target 25. This is generally well known standard practice for creating virtual depth in a VR environment of the screen 12. The VR stimulus software for performing the tests of the present invention is integrated into existing vestibular/neurological software for protocol setup, test results analysis, and to create VR stimulus 25.

Disparity Fusion (Vergence Saccade) Testing

One vergence test, the representative results of which are shown in FIG. 6, of the present invention will present targets 25 at different virtual depths in a punctuated fashion (sudden shifts in target position followed by delays where the targets are stationary), which are referred to here as Vergence Step, or vergence saccade or disparity fusion. This saccadic vergence stimulus 25 pattern will encourage subjects to make responsive convergence/divergence eye movements (schematically represented in traces 130 and 140) to fuse the stimuli 25 into a single perceived image or target 25 and then hold that vergence position until the next stimulus change. This disparity fusion test can be summarized as where subjects visualize the stimulus 25 moving towards and away from them in a saccadic manner. The following variables were our key measures: Left and right eye Decay time (also called response time), Symmetry of left and right eye movement, Amplitude of-Eye movement, and % of saccade. The I-Portal google system from Neurokinetics is sufficient for this testing, however for other platforms the sampling rate of the eye images should be 100 hz (or higher) with a resolution of <0.1°. The testing platform 18 was designed to track 18 variables associated with specific physiologic responses for this test, with the major variables being noted, however any desired variable may be tracked if the system 10 contains sufficient information. For example measurements of the maximum left and right eye acceleration will be subject to the restraints of the sampling rate.

For Vergence Step testing, data will be segmented so that each segment or cycle is the eye response to a target 25 shift. Measures will be derived both for individual segments and for the testing data as a whole. The following are examples of measures that will be generated by the method or device for Vergence Step testing, both per segment and for the whole test: The correlation between the movement of the two eyes in response to the target shift, where "correlation" could be any new or standard method of measuring how the two eye signals are alike, or co-vary (examples: Pearson's correlation, Kendall's Tau, Spearman, or any form of cross-correlation, e.g., correlations at different respective offsets of the two signals); The presence and amount of saccadic movement (which is distinct from vergence movement), The time for each eye to respond to target change and reach a steady position, The magnitude of the vergence movement of each eye, and The asymmetry, between the two eyes, of any of the previous three measures (saccades, time, magnitude).

FIG. 6 specifically is a graph of an mTBI subject and a control subject response to a vergence saccade test performed on the head mounted display 10 of the vergence testing platform 100 of FIG. 1. Specifically the mTBI subject was a 20 year old female with the testing performed 2 days after she sustained the injury causing her mTBI. The upper graph shows the position of the target or stimulus 25 jumping between two positions with the trace of the mTBI subject's right eye 130 and left eye 140 shown. This evidences the abnormal state in which the left and right eyes are moving in parallel with a symmetry, specifically the inward symmetry (comparison of left to right eye movement in response to presentation of the target 25 at the position "closest" to the subject) of the mTBI subject was 0.71 and the outward symmetry (comparison of left to right eye movement in response to presentation of the target 25 at the position "farthest" to the subject) of the mTBI subject was 0.88. This is also described as conjugate motion. The lower graph shows the position of the target or stimulus 25 jumping between the same two positions as the upper graph (as it is the same test) with the trace of the control subject's right eye 130 and left eye 140 shown. The control subject was a 32 year old male whose response evidences the generally normal state in which the left and right eyes are moving in opposition to each other with a symmetry of at or near −1.0, specifically the inward symmetry (comparison of left to right eye movement in response to presentation of the target 25 at the position "closest" to the subject) of the control subject was −0.97 and the outward symmetry (comparison of left to right eye movement in response to presentation of the target 25 at the position "farthest" to the subject) of the control subject was −0.91. This is also described as disconjugate motion. A normal symmetry result for this test approaches −1.0 while abnormal symmetry for this test is typically above 0.

FIG. 11 shows a summary of results from subjects of this saccadic vergence test. In this particular sample there were 58 control subjects analyzed, specifically 42 males (72.4%) and 16 females (27.6%), ranging in age from 22-45 with a mean of 30.5 years (SD 6.8 years). Additionally in this sample there were 17 total concussed subjects analyzed, specifically 13 males (76.5%) and 4 females (23.5%), ranging in age from 20-43 with a mean of 29.1 years (SD 8.1 years). All mTBI subjects and controls were tested at three sites: University of Miami Miller School of Medicine; Madigan Army Medical Center; and Naval Medical Center San Diego. All mTBI subjects were diagnosed with mTBI by an emergency room physician. mTBI subjects tested using the following time line: 24-48 hours post injury; 1 week post injury and 2 weeks post in jury. All control subjects were tested one time.

Figure 7:
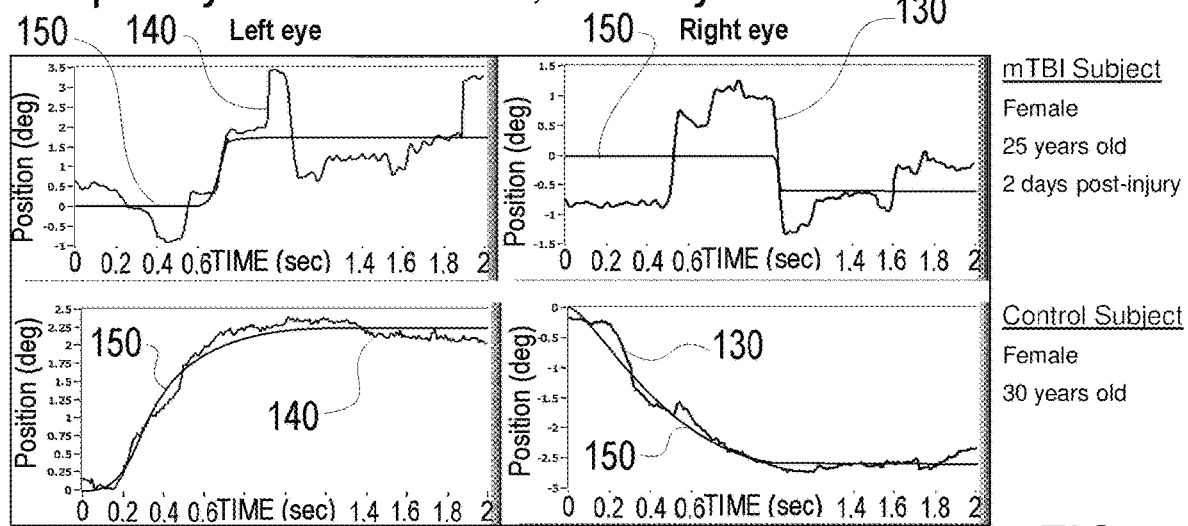
FIG. 7 is a graph of mTBI subject and control subject average eye response to the vergence saccade test of FIG. 6.
Figures 8, 9, 10:
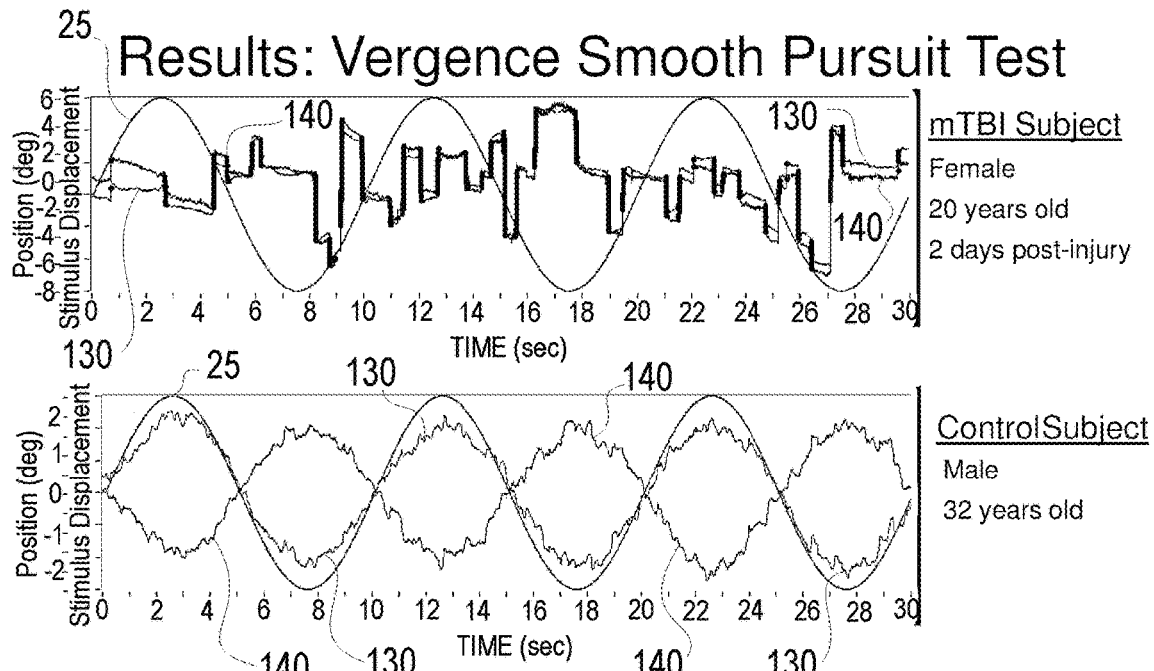
FIG. 8 is a chart of mTBI subject and control subject average eye response times and amplitudes to the vergence saccade test of FIG. 6.
FIG. 9 is a graph of mTBI subject and control subject response to a vergence smooth pursuit test performed on the head mounted display of the vergence testing platform of FIG. 1.
FIG. 10 is a chart of summary of results of the mTBI subject and control subject eye responses to the vergence smooth pursuit test of FIG. 9.

FIG. 7 is a graph of an mTBI subject and a control subject average eye response over multiple trials to the vergence saccade test of FIG. 6. In this graph the mTBI subject is a 25 year old female with the test undertaken 2 days post injury. The control is a 30 year old female. FIG. 8 is a chart of mTBI subject and control subject decay times (a measure of response) and amplitudes to the vergence saccade test of FIG. 6 and the test subjects shown in FIG. 7. It is readily apparent that the curves are different between the two subjects in how closely they match the graph of NL physiologic response 150. As as seen in the table of FIG. 8, significantly higher values for decay time and significantly lower values for eye amplitude were seen in both inward and outward target movement for the mTBI subject compared to the control subject Vergence Smooth Pursuit Testing Another vergence test of the method or device 100 will present a continuously, smoothly transitioning movement of the stimuli 25, creating the appearance of a target 25 gradually moving toward or away from the subject in the virtual depth space. This will encourage subjects to make continually updated, smoothly transitioning convergence and divergence movements. Here we refer to this as "Vergence Pursuit" or vergence smooth pursuit. For the vergence smooth pursuit test, subjects visualized the stimulus 25 moving towards and away in a sinusoidal pattern at 0.1 Hz. The following variables were determined to be key variables for analysis, namely Near and far angle (measures of the angle of the left and right eye with the target 25 at the nearest point and the farthest point, respectively, in its sinusoidal movement), Excursion (a measure of the difference between the near and far angle, or an amplitude measurement), Lag time (a measure of the delay between target movement and tracking eye movement) and Symmetry (a measure of the comparison of the left and the right eye movements).

For Vergence Pursuit testing, data will be both segmented into individual cycles (sub-segments of the target movement profile, e.g., cycles of a sinusoidally-modulated stimulus) and analyzed per cycle, or analyzed for the whole test. The following are examples of measures that will be generated by the method or device for Vergence Pursuit testing, both per cycle and for the whole test: The correlation between the movements of the two eyes during target presentation (where "correlation" or symmetry is as defined for Vergence Step testing above); The lag (temporal shift) of the eye movement relative to the virtual position of the stimulus; The amplitude or gain of the eye position relative to the virtual position of the stimulus at any or all time points during the test; The presence and amount of saccadic movement during the test; and The asymmetry, between the two eyes, of any of the previous three measures (saccades, lag, gain).

FIG. 9 is a graph of an mTBI subject and a control subject responses to a vergence smooth pursuit test performed on the head mounted display 10 of the vergence testing platform 100 of FIG. 1. FIG. 10 is a chart of summary of results of the mTBI subject and control subject eye responses to the vergence smooth pursuit test of FIG. 9. Specifically the mTBI subject was a 20 year old female with the testing performed 2 days after she sustained the injury causing her mTBI, while the control was a 32 year old male. A cursory review of the two graphs makes clear that the eye movement (curves) between the two subjects are quite different. Note in the table, the near normal symmetry value of the control subject approaching −1.0 (−0.91) compared to the mTBI subject's value greater than +0.9. Additionally, small lag values are seen for the control subject while significantly larger values are seen in the mTBI subject.

FIG. 11 is a chart summarizing symmetry results for mTBI subjects and control subjects for a series of vergence testing performed on the head mounted display of the vergence testing platform of FIG. 1. Analysis of variance noted a high degree of vergence symmetry deficits in the mTBI group that were not present in the control group with p values less 0.001 for both disparity fusion symmetry and vergence smooth pursuit symmetry.

Logistic regression analysis of this data for both vergence tests shown in FIGS. 12 and 13 demonstrated that abnormalities were virtually non-existent in control subjects and present in about half of mTBI subjects. A 95% confidence interval for symmetry values in control subjects fell in the range of −1.0 to −0.87. The presence of any vergence abnormalities in the testing paradigm was largely diagnostic of mTBI, in other words abnormal results were essentially only seen in mTBI subjects. FIGS. 12 and 13 are charts summarizing linear regression analysis as a predictor of mTBI using the results of the vergence testing performed on the head mounted display of the vergence testing platform of FIG. 1.

Figure 14:
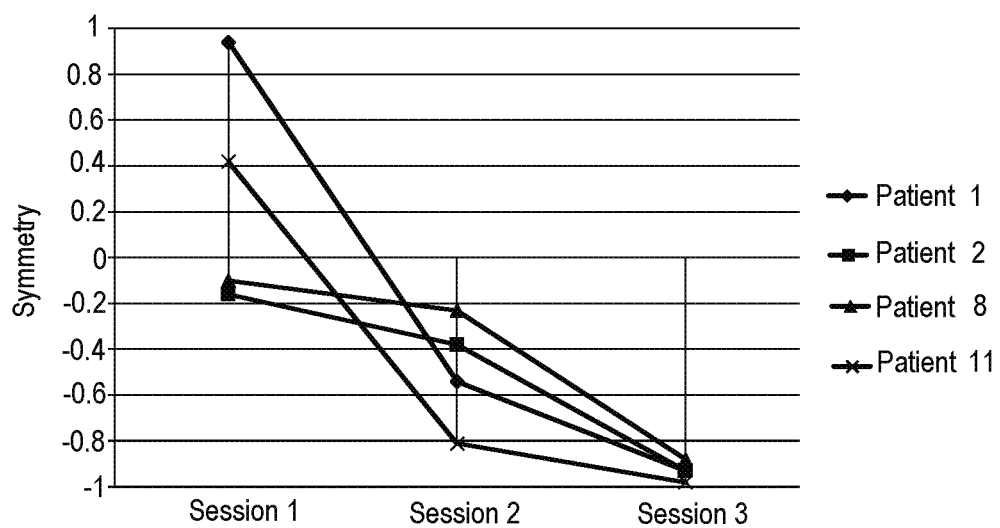
FIG. 14 is a chart of smooth pursuit vergence testing symmetry of four mTBI subjects over a two week period using the results of the smooth pursuit vergence testing performed on the head mounted display of the vergence testing platform of FIG. 1.

FIG. 14 is a chart of smooth pursuit vergence testing symmetry of four mTBI subjects over a two week period using the results of the smooth pursuit vergence testing performed on the head mounted display of the vergence testing platform of FIG. 1. As shown in FIG. 14, significant improvement in results compared with control levels was exhibited in these subjects over a two week period.

Vergence deficiencies can be objectively measured and characterized using the portable, 3D head mounted display system 100 with integrated eye tracking technology. Characterizing vergence function in healthy controls and pathologic dysfunction in mTBI patients as evidenced herein is an additional tool in the management and study of individuals with mTBI. Vergence data may be used as a tool in the diagnosis of mTBI and return to activity decision making.

Objective Measurement of Minimal Vergence Angle (Minimal Vergence Distance)

The vergence testing platform 100 of FIG. 1 using the smooth pursuit vergence testing provides for objective measurement of minimal vergence angle or minimal vergence distance. The minimal vergence angle or minimal vergence distance is the point where the subject's eyes no longer resolve a single target such that the subject generally will begin to see two stimuli. The minimal vergence angle is the angle of the eye at this point and will correspond to a minimal vergence distance in front of the subject. In prior art mechanical vergence systems the subject may be prompted to indicate when they see two stimuli or targets as a target is advanced toward the subject in order to attempt to measure this physiologic parameter of minimal vergence angle or distance. In the present platform 100, the subjects eye responses throughout the above smooth pursuit vergence testing can be tracked and eye oscillations above a threshold can be used as an indication of the subject reaching minimal vergence angle. The platform yields an objective measure for this physiologic parameter.

Offset Vergance Testing

A further variation to the first two tests is the alignment of the target 25. In the illustrated example above the target 25 is virtually aligned between the two eyes, generally a standard in vergence testing, and the movement is along a horizontal line (Line of Testing). In the present invention, either of the first two tests (VERGENCE SMOOTH PURSUIT and VERGENCE SACCADE) may have the alignment of the Line of Test shifted from this center position. Of particular interest is an alignment of the Line of Test of the test target 25 with one or the other eye (e.g., a horizontal offsetting of the location of the Line of Test of the test target 25 from the center location) and performing the vergence smooth pursuit and vergence saccade type vergence testing with a Line of Test aligned with one or the other eye. Such an eye aligning offsetting of the Line of Test will greatly affect the normal symmetry for either the vergence smooth pursuit and the vergence saccade type vergence testing, but such placement can increase the magnitude of results for one of the eyes, such as the near and far angle of the eye that is not aligned with the target 25. This can be particularly helpful in obtaining objective measurements for the objective measurement of minimal vergence angle for each eye independently of the other.

The performance of the vergence testing with the Line of Test positioning aligned with one eye can also isolate other issues with results from the aligned eye. For example if the eye that is aligned with the target 25 jumps off target 25 with a saccadic movement, then it is not the aligned eye's vergence movement that in error as no eye movement was necessary for at least that eye in this movement. These modifications of the vergence smooth pursuit and vergence saccade type vergence testing are called offset vergence testing. This type of offset vergence testing yields improved assessment of subject thresholds and better comparisons of left and right eye disparities.

Vertically Adjusted Vergance Testing

The adjustment of the horizontal Line of Test for vergence smooth pursuit and vergence saccade type vergence testing along a horizontal plane forms the offset vergence testing described above and is useful for isolating single eye movements as discussed above. The present invention further provides for adjustment or movement of the horizontal Line of Test for vergence smooth pursuit and vergence saccade type vergence testing from the conventional center positon along a vertical plane forms a distinct testing known herein as Vertically Adjusted Vergence Testing. Performing Vertically Adjusted Vergence Testing, both above and below the center of vision, can be used to enhance measured discrepancies between left and right eye movements of the subject.

Typical vertical adjustment would be expected to be at least 10 degrees above or below center to yield significant additional physiologic parameters for the subject.

The Vertically Adjusted Vergence Testing can be combined with the offset vergence testing described above to have the horizontal Line of Test for vergence smooth pursuit and vergence saccade type vergence testing aligned along a vertical plane through a subject's eye but adjusted above or below the center of vision, however the alignment no longer eliminates the eye movement of the aligned eye in such testing due to the inclusion of the vertical offset of the line of test.

Full 3-Dimensional Vergence Testing

The vergence testing on the platform 100 is not limited to the specific examples discussed above in which the target 25 movement along the Line of Test within a vergence test is maintained within a general horizontal line. A further vergence test of the method or device 100 will present either of the vergence smooth pursuit and vergence saccade type vergence testing in combination with additional horizontal and/or vertical movement that will create the impression of a target 25 that moves both in depth relative to, and in position within the visual plane (i.e. this will create a target 25 that moves virtually in all three dimensions). In short the Line of Test is no longer in a horizontal line extending ONLY toward and away from the subject. The Line of Test may be angled up or down or sideways. Further the Line of Test need not be a straight line but could form a curved trace or even a loop shape.

This form of testing is referred to herein as "Full 3-Dimensional Vergence". As one example instance, a test could be presented in which the target moves smoothly along a virtual trajectory through all 3 spatial dimensions, tracing a circle, ellipse, spiral, or any other trajectory that is at any angle to the visual plane, or that continuously changes angle relative to the visual plane.

Objective Testing of Vergence Dysfunction

The above described invention provides an objective testing of vergence dysfunction comprising the steps of: providing a head mounted goggle based stimulus generating eye tracking unit to the subject; presenting visual stimulus to the subject, wherein the visual stimulus is in the head mounted goggle based system and forms the optical target stimulus for at least one vergence test; obtaining objective physiologic response of the subject from the head mounted goggle unit based upon each of the visual stimulus presented to the subject in each test; and using the objective physiologic responses to diagnose the presence of vergence dysfunction.

A portable objective testing platform for vergence testing 100 may be summarized as including a laptop 50; and a head mounted goggle based stimulus generating eye tracking unit 10 coupled to the laptop 50, the unit 10 including a VR screen 12 and two cameras 16 for recording eye movement, wherein the VR screen 12 is configured to present visual stimulus 25 to the subject, wherein the visual stimulus 25 is in the head mounted goggle based system 10 and forms the optical target stimulus 25 for at least one vergence test, and wherein the cameras 16 are configured to obtain objective physiologic responses of the subject from the head mounted goggle unit 10 based upon each of the visual stimulus 25 presented to the subject in each test.

Vergence Recovery Convalescence

Another aspect of the present invention is the provision of vergence recovery convalescence using the dynamic vergence testing platform 100 including 3d head mounted display system 10 with integrated eye tracking technology comprising the steps of: A. providing a head mounted goggle based stimulus generating eye tracking unit 10 to the subject; B. presenting visual stimulus 25 to the subject, wherein the visual stimulus 25 is in the head mounted goggle based system 10 and forms the optical target stimulus 25 for at least one vergence test; C. obtaining objective physiologic response of the subject from the head mounted goggle unit 10 based upon each of the visual stimulus 25 presented to the subject in each test; and D. Presenting at least select physiologic response to the subject; and E. Repeating steps B-D.

Subjects with vergence dysfunction are greatly aided when the nature of the dysfunction is explained and they have an opportunity to "work" on the identified deficiency in the course of further vergence testing. The offset vergence testing protocols described herein may be particularly well suited for isolating the eyes requiring the work to facilitate convalescence using the dynamic vergence testing platform 100. Once a deficiency is noted the subject can be given threshold for a given deficiency in a given test with the testing protocol repeated until the subject reaches the given threshold for the session (or lack of improvement is noted after a given testing time). A new threshold is set for subsequent sessions. The positive feedback of reaching improved results can facilitate subject gains over time.

It is understood, therefore, that this invention is not limited to the particular embodiments disclosed, but it is intended to cover modifications that are within the spirit and scope of the invention, as defined by the appended claims and equivalents thereto. The preferred embodiments described above are illustrative of the present invention and not restrictive hereof. It will be obvious that various changes may be made to the present invention without departing from the spirit and scope of the present invention. The precise scope of the present invention is defined by the appended claims and equivalents thereto.

What is claimed is:

1. An objective testing of vergence dysfunction comprising the steps of:
   providing a head mounted goggle based stimulus generating eye tracking unit to the subject;
   presenting visual stimulus to the subject, wherein the visual stimulus is in the head mounted goggle based system and forms the optical target stimulus for at least one vergence test, wherein at least one vergence test comprises a saccade vergence test that includes presenting targets at different virtual depths in a punctuated fashion whereby sudden shifts in target position are presented to the subject followed by delays where the targets are stationary;
   obtaining objective physiologic response of the subject from the head mounted goggle unit based upon each of the visual stimulus presented to the subject in each test; and
   using the objective physiologic responses to diagnose the presence of vergence dysfunction.

2. The objective testing of vergence dysfunction according to claim 1 wherein the optical target stimulus is presented in the context of background stimuli configured to appear as 3 dimensional objects that surround and orientate the target stimulus in virtual 3 dimensional space.

3. The objective testing of vergence dysfunction according to claim 2 wherein the background stimuli is in the form of a box tunnel.

4. The objective testing of vergence dysfunction according to claim 1 wherein the objective physiologic responses used to diagnose the presence of vergence dysfunction includes Left and right eye response time to saccade vergence tests.

5. The objective testing of vergence dysfunction according to claim 1 wherein the objective physiologic responses used to diagnose the presence of vergence dysfunction includes Symmetry of left and right eye movement of saccade vergence tests.

6. The objective testing of vergence dysfunction according to claim 1 wherein the objective physiologic responses used to diagnose the presence of vergence dysfunction includes at least one of i) Left and right eye response time to saccade vergence tests, ii) Symmetry of left and right eye movement of saccade vergence tests, iii) Amplitude of-Eye movement of saccade vergence tests, and iv) % of saccade of saccade vergence tests.

7. An objective testing of vergence dysfunction comprising the steps of:
providing a head mounted goggle based stimulus generating eye tracking unit to the subject;
presenting visual stimulus to the subject, wherein the visual stimulus is in the head mounted goggle based system and forms the optical target stimulus for at least one vergence test, wherein at least one vergence test comprises a smooth pursuit vergence test that includes presenting a continuously, smoothly transitioning movement of the stimuli configured to create the appearance of a target gradually moving toward or away from the subject in the virtual depth space;
obtaining objective physiologic response of the subject from the head mounted goggle unit based upon each of the visual stimulus presented to the subject in each test; and
using the objective physiologic responses to diagnose the presence of vergence dysfunction.

8. The objective testing of vergence dysfunction according to claim 7 wherein the smooth pursuit vergence test comprises having subjects visualized the stimulus moving towards and away in a sinusoidal pattern at about 0.1 Hz.

9. The objective testing of vergence dysfunction according to claim 7 wherein the objective physiologic responses used to diagnose the presence of vergence dysfunction includes at least one of i) measures of the angle of the left and right eye with the target at the nearest point and the farthest points in its sinusoidal movement in the smooth pursuit vergence testing, ii) a measure an amplitude of eye movement in the smooth pursuit vergence testing, iii) Lag time which is a measure of the delay between target movement and tracking eye movement in the smooth pursuit vergence testing, and iv) Symmetry which is a measure of the comparison of the left and the right eye movements in the smooth pursuit vergence testing.

10. An objective testing of vergence dysfunction comprising the steps of:
providing a head mounted goggle based stimulus generating eye tracking unit to the subject;
presenting visual stimulus to the subject, wherein the visual stimulus is in the head mounted goggle based system and forms the optical target stimulus for at least one vergence test, wherein at least one vergence test comprises an offset vergence test wherein the optical target stimulus is presented in a line offset from the midline between the subject's eyes;
obtaining objective physiologic response of the subject from the head mounted goggle unit based upon each of the visual stimulus presented to the subject in each test; and
using the objective physiologic responses to diagnose the presence of vergence dysfunction.

11. The objective testing of vergence dysfunction according to claim 10 wherein at least offset vergence test includes aligning the target with one of the subject's eyes.

12. The objective testing of vergence dysfunction according to claim 10 wherein using the objective physiologic responses to diagnose the presence of vergence dysfunction is used to diagnose mTBI.

13. The objective testing of vergence dysfunction according to claim 1 wherein using the objective physiologic responses to diagnose the presence of vergence dysfunction is used to diagnose mTBI.

14. The objective testing of vergence dysfunction according to claim 7 wherein using the objective physiologic responses to diagnose the presence of vergence dysfunction is used to diagnose mTBI.

15. The objective testing of vergence dysfunction according to claim 7 wherein the optical target stimulus is presented in the context of background stimuli configured to appear as 3 dimensional objects that surround and orientate the target stimulus in virtual 3 dimensional space.

16. The objective testing of vergence dysfunction according to claim 15 wherein the background stimuli is in the form of a box tunnel.

17. The objective testing of vergence dysfunction according to claim 10 wherein the optical target stimulus is presented in the context of background stimuli configured to appear as 3 dimensional objects that surround and orientate the target stimulus in virtual 3 dimensional space.

18. The objective testing of vergence dysfunction according to claim 10 wherein the background stimuli is in the form of a box tunnel.

* * * * *